United States Patent [19]

VandenBerg

[11] Patent Number: Plant 7,423

[45] Date of Patent: Jan. 15, 1991

[54] CHRYSANTHEMUM PLANT NAMED YELLOW ENVY

[75] Inventor: Cornelis P. VandenBerg, Salinas, Calif.

[73] Assignee: Yoder Brothers, Inc., Barberton, Ohio

[21] Appl. No.: 388,893

[22] Filed: Aug. 2, 1989

[51] Int. Cl.[5] ..... A01H 5/00

[52] U.S. Cl. ..... Plt./78

[58] Field of Search ..... Plt./74, 77, 78

[56] References Cited

U.S. PATENT DOCUMENTS

P.P. 5,986 5/1987 Duffett ..... Plt. 77

OTHER PUBLICATIONS

Gosling S. G. (ed.), "Appendix II", *The Chrysanthemum Manual*, Essex Telegraph Press, Ltd., Colchester, U.K. 1979, pp. 329, 330.

Searle, S. A. et al., "Use of Gamma and X-Rays", *Chrysanthemums the Year Round*, Blandford Press, London, U.K., 1968, pp. 27-29.

Broertjes, C., P. Koene and J. W. H. Van Veen, "A Mutant of a Mutant of a Mutant of a . . . Irradiation of Progressive Radiation-Induced Mutants in a Mutation-Breeding Programme with Chrysanthemum Morifolium Ram.", *Euphytica*, 29 (1980): 525-530.

Teynor, Tim M., Peter D. Ascher, R. E. Widmer and J. J. Luby, "Inheritance of Flower Color in *Dendranthema grandiflora* Tzvelev. (Chrysanthemum morifolium Ramat.) Using Cultivars and Inbreds. I. Plastid Pigmentation", *Euphytica*, 42 (1989): 199-207, Kluwer Academic Publishers, Netherlands.

Teynor, Tim M., Peter D. Ascher, R. E. Widmer and J. J. Luby, "Inheritance of Flower Color in *Dendranthema grandiflora* Tzvelev. Chrysanthemum morifolium Ramat.) Using Cultivars and Inbreds. II. Vacuole Pigmentation", *Euphytica*, 42 (1989): 297-305, Kluwer Academic Publishers, The Netherlands.

Broertjes, C., "Mutation Breeding of Chrysanthemums", *Euphytica*, 15 (1966): 156-162, Association Euratom-Ital, Wageningen.

Chan, A. P., "Chrysanthemum and Rose Mutations Induced by X Rays", Reprinted from Proceedings of the American Society for Horticultural Science, vol. 88, 1966, Plant Research Institute, Research Branch, Canada Dept. of Agriculture, Ottawa, Canada, pp. 613-620.

Broertjes, C. and A. M. Van Harten, *Application of Mutation Breeding Methods in the Improvement of Vegetatively Propagated Crops*, "Chrysanthemum", Elsevier Scientific Publishing Company, Amsterdam-Oxford-New York, 1978, pp. 162-175.

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Yellow Envy particularly characterized by its flat capitulum form, decorative capitulum type, yellow ray floret color, diameter across face of capitulum of up to 13 cm at maturity when grown as a pinched disbudded pot mum, uniform eight week photoperiodic flowering response to short days, short plant height when grown as a pinched pot mum, and spreading branching pattern.

3 Drawing Sheets

---

The present invention comprises a new and distinct cultivar of Chrysanthemum, botanically known as *Dendranthema grandiflora*, and referred to by the cultivar named Yellow Envy.

Yellow Envy, identified as 82-E64B07, is a product of a mutation induction program which had the objective of creating new Chrysanthemum cultivars that would expand the color range of an existing cultivar while retaining all other traits.

Yellow Envy was discovered and selected by a technician working under formulations established by Cornelis P. VandenBerg in February of 1986 in a controlled environment in Alva, Fla. as one flowering plant within a flowering block established as rooted cuttings from stock plants which had been exposed as unrooted cuttings to an X-ray source of 2000 rads. The irradiated parent was the cultivar identified as Envy, disclosed in U.S. Plant Pat. No. 5,986.

The first act of asexual reproduction of Yellow Envy was accomplished when vegetative cuttings were taken from the initial selection in April of 1986 in a controlled environment in Alva, Fla., by technicians working under formulations established by Cornelis P. VandenBerg.

Horticultural examination of controlled flowerings of successive plantings has shown that the unique combination of characteristics as herein disclosed for Yellow Envy are firmly fixed and are retained through successive generations of asexual reproduction.

Yellow Envy has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Yellow Envy, which, in combination, distinguish this Chrysanthemum as a new and distinct cultivar:

1. Flat capitulum form.
2. Decorative capitulum type.
3. Yellow ray floret color.

4. Diameter across face of capitulum up to 13 cm at maturity, when grown as a pinched disbudded pot mum.

5. Uniform eight week photoperiodic flowering response to short days.

6. Short plant height, requiring 7 to 14 long days after pinch prior to short days and 1 application of 2500 ppm B-9 SP to attain a flowered plant height of 25 to 35 cm for year-round flowerings when grown as a pinched pot mum.

7. Spreading branching pattern.

The accompanying photographic drawing show typical inflorescence and leaf characteristics of Yellow Envy, with the colors being as nearly true as possible with illustrations of this type. Sheet 1 is a color photograph of Yellow Envy grown as a pinched disbudded pot mum. Sheet 2 is a black and white photograph of three views of the inflorescence of Yellow Envy. Sheet 3 is a black and white photograph showing the upper and under sides of the leaves of Yellow Envy at three stages of development (mature, intermediate and immature).

Of the commercial cultivars known to the inventor, the most similar in comparison to Yellow Envy is the parent cultivar Envy. All traits of Yellow Envy are similar to those of Envy, except the color of ray florets. Yellow Envy has a yellow ray floret color, while the color of Envy is ivory and white.

In the following description color references are made to The Royal Horticultural Society Color Chart. The color values were determined on plant material grown as a pinched disbudded pot mum in Salinas, Calif. on Apr. 3, 1989.

Classification:

*Botanical.*—*Dendranthema grandiflora* cv Yellow Envy.

*Commercial.*—Decorative disbud pot mum.

INFLORESCENCE

A. Capitulum:

*Form.*—Flat.

*Type.*—Decorative.

*Diameter across face.*—Up to 13 cm at maturity.

B. Corolla of ray florets:

*Color (general tonality from a distance of three meters).*—Yellow.

*Color (upper surface).*—3B at the center of the inflorescence to 3D at the outer margins of the ray florets.

*Color (under surface).*—3D.

*Shape.*—From spooned to fully flat, with up to 50% of the ray florets at the outer margins thereof being spoon shaped, with the spoon length ranging from 20% to 100% of the total ray floret length.

C. Corolla of disc florets:

*Color (mature).*—2B.

*Color (immature).*—154A.

D. Reproductive organs:

*Androecium.*—Present on disc florets only; scant pollen.

*Gynoecium.*—Present on both ray and disc florets.

PLANT

A. General appearance:

*Height.*—Short; 25 to 35 cm as a pinched disbudded pot mum with 7 to 14 long days after pinch prior to short days and 1 application of 2500 ppm B-9 SP.

*Branching pattern.*—Spreading.

B. Foliage:

*Color (upper surface).*—147A.

*Color (under surface).*—147B.

*Shape.*—Lobed and moderately serrated.

I claim:

1. A new and distinct Chrysanthemum plant named Yellow Envy, as described and illustrated.

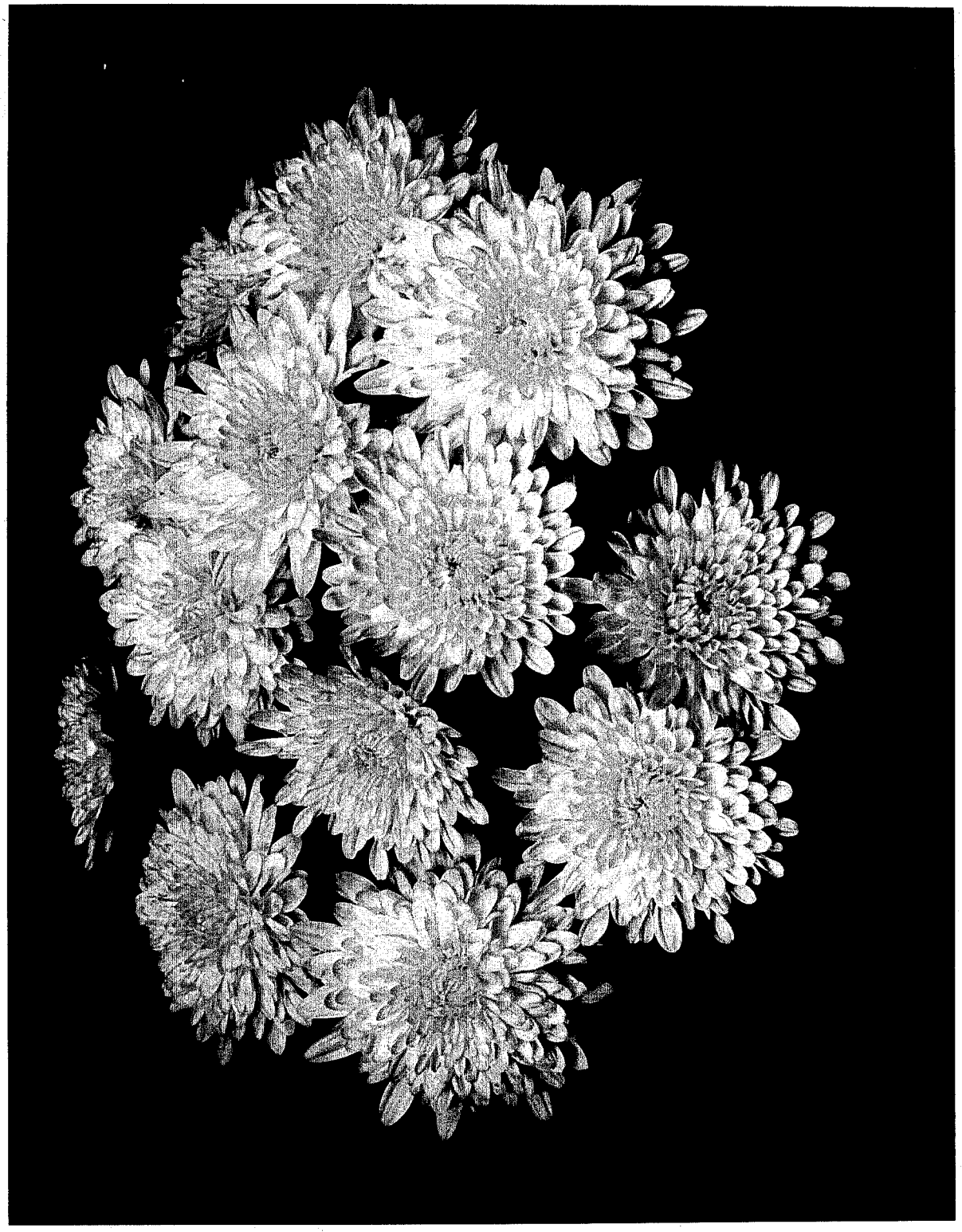

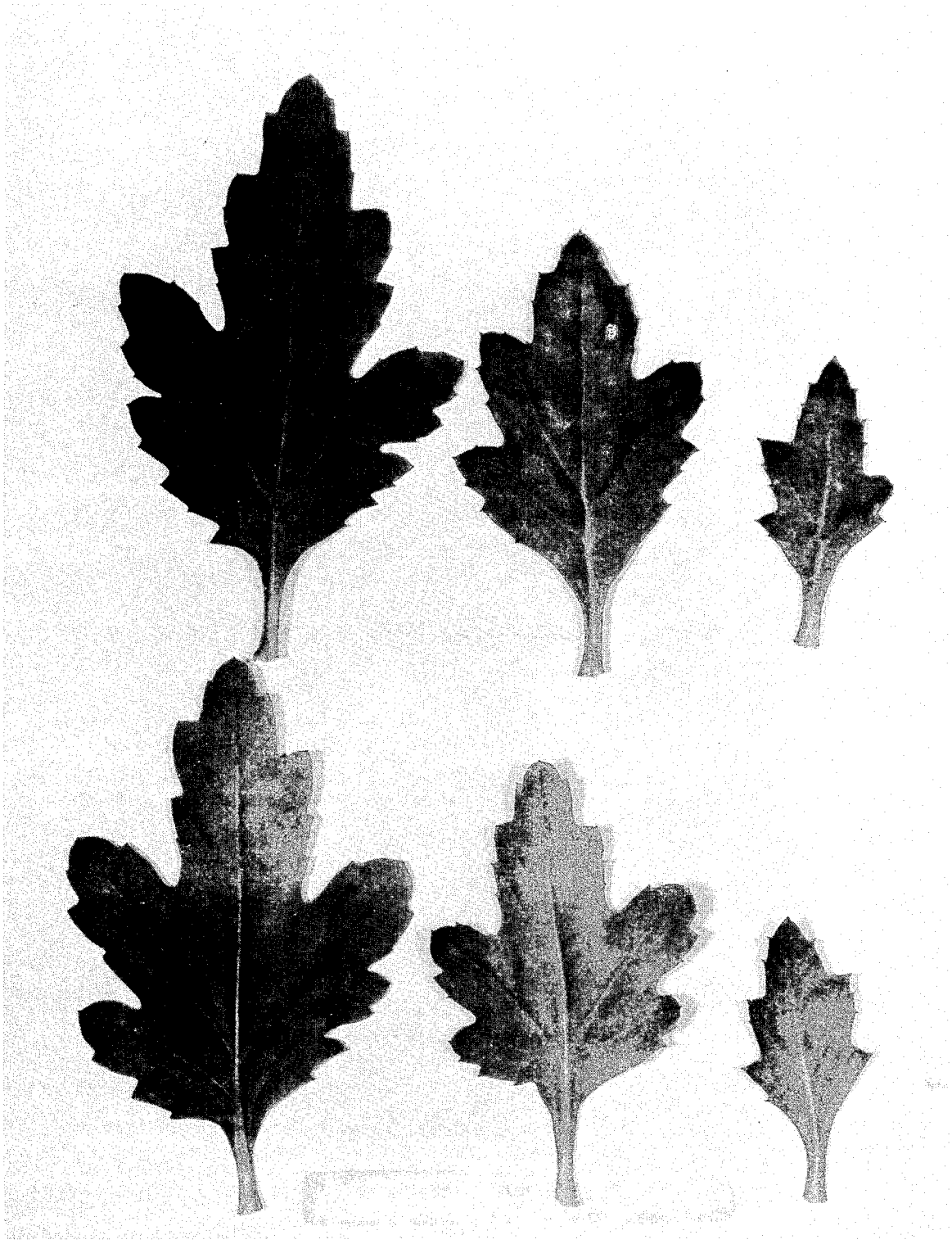

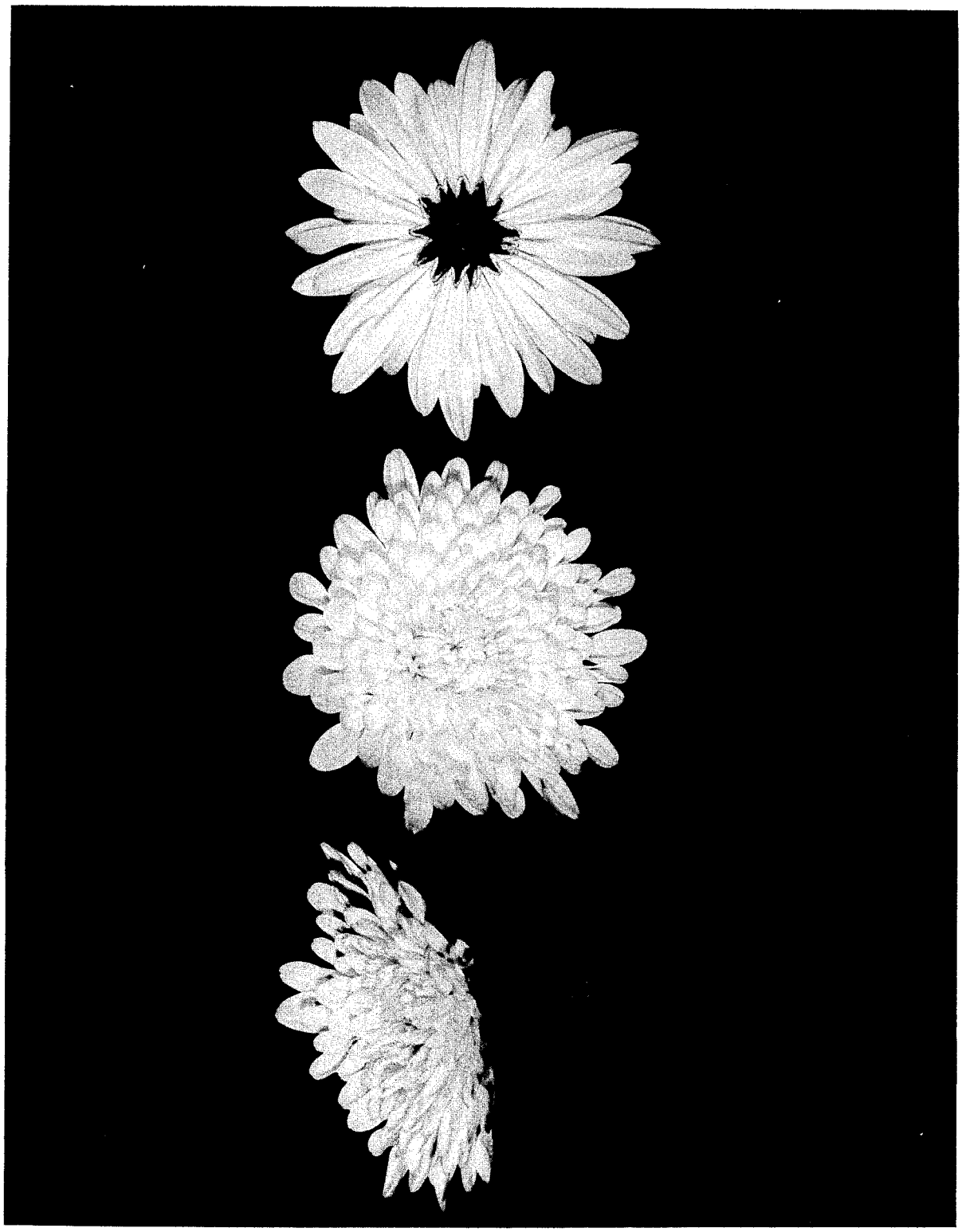

* * * * *